United States Patent

Sakakibara et al.

[11] 4,086,221
[45] Apr. 25, 1978

[54] POLYPEPTIDES AND PROCESS FOR PRODUCING THE SAME

[75] Inventors: Shumpei Sakakibara, Suita; Tadanori Morikawa, Takatsuki; Eisuke Munekata, Toyonaka; Terutoshi Kimura, Takarazuka; Yasuo Nakagawa, Nishinomya; Toshiharu Noda, Toyonaka, all of Japan

[73] Assignee: Toyo Jozo Kabushiki Kaisha, Japan

[21] Appl. No.: 682,752

[22] Filed: May 3, 1976

[30] Foreign Application Priority Data

May 1, 1975    Japan .................................. 50-52064

[51] Int. Cl.² ..................... C07C 103/52; A61K 37/00
[52] U.S. Cl. .............................. 260/112.5 T; 424/177
[58] Field of Search ................... 260/112.5 T; 424/177

[56] References Cited

U.S. PATENT DOCUMENTS

| | | | |
|---|---|---|---|
| 3,798,203 | 3/1974 | Brugger et al. | 260/112.5 T |
| 3,891,614 | 6/1975 | Sakakibara et al. | 260/112.5 T |

OTHER PUBLICATIONS

J. Med. Chem., 18, (1975), pp. 124–126.

Primary Examiner—Delbert R. Phillips
Attorney, Agent, or Firm—Young & Thompson

[57] ABSTRACT

Polypeptides of the formula

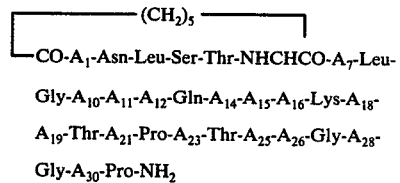

wherein $A_1$ is Ser or Gly, $A_7$ is Val or Met, $A_{10}$ is Lys or Thr, $A_{11}$ is Leu or Tyr, $A_{12}$ is Ser or Thr, $A_{14}$ is Glu or Asp, $A_{15}$ is Leu or Phe, $A_{16}$ is His or Asn, $A_{18}$ is Leu or Phe, $A_{19}$ is Gln or His, $A_{21}$ is Tyr or Phe, $A_{23}$ is Arg or Gln, $A_{25}$ is Asp or Asn or Ala, $A_{26}$ is Val or Thr or Ile, $A_{28}$ is Ala or Ser or Val, and $A_{30}$ is Thr or Val or Ala, and pharmaceutically acceptable acid addition salts and complexes, have serum calcium reducing activity.

3 Claims, No Drawings

POLYPEPTIDES AND PROCESS FOR PRODUCING THE SAME

This invention relates to novel polypeptides of the formula

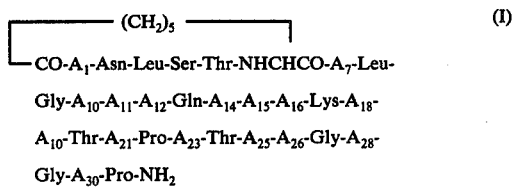 (I)

wherein $A_1$ is Ser or Gly, $A_7$ is Val or Met, $A_{10}$ is Lys or Thr, $A_{11}$ is Leu or Tyr, $A_{12}$ is Ser or Thr, $A_{14}$ is Glu or Asp, $A_{15}$ is Leu or Phe, $A_{16}$ is His or Asn, $A_{18}$ is Leu or Phe, $A_{19}$ is Gln or His, $A_{21}$ is Tyr or Phe, $A_{23}$ is Arg or Gln, $A_{25}$ is Asp or Asn or Ala, $A_{26}$ is Val or Thr or Ile, $A_{28}$ is Ala or Ser or Val, and $A_{30}$ is Thr or Val or Ala, and acid addition salts and complexes thereof.

The polypeptides of formula [I] have serum calcium reducing activity.

Calcitronin is a well-known polypeptide having mammalian serum calcium reducing activity, and is isolated from mammalian thyroid gland or avian or piscine ultimo branchial body. The amino acid sequence of the calcitonin depends on the origin of the species and synthetic calcitonins having the same chemical structure as those of natural origin have recently become known.

The calcitonins of natural origin such as eel-, salmon- or human-calcitonin are polypeptides consisting of 32 amino acids, wherein the first and 7th amino acids are L-cysteine and the mercapto group thereof is bonded to comprise a disulfide bridge.

The polypeptide of the present invention has neither first nor seventh amino acid L-cysteine and the said L-cysteine is replaced by alpha-aminosuberic acid of the formula;

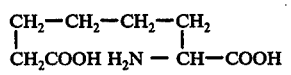

The carboxyl group at ω-position is bonded with N-terminal amino acid to form a ring structure.

These novel compounds have important therapeutic properties, and may be prescribed for the purpose of reducing serum calcium content in diseases such as hypercalcemia, an endogenous calcitonin deficiency disease caused by dysthyroidism or hyperparathyroidism. The novel compound can be prescribed for osteopathy requiring calcium, such as osteoporosis, ostermalacia, fracture, fibrous dysplasia of the bone or rachitis caused by corticosterone therapy or inactivation after menopause or external injury, and is especially suited to therapy in combination with calcium or phosphorus. Also, the novel product can be used for therapy of Paget's disease and for therapy or prevention of peptic ulcer. The compound of the present invention is more stable in serum, liver or kidney than the known calcitonins, and is more stable in the purification process or storage, due to lack of disulfide linkage. The activity of some of the polypeptides of the formula [I] is the same or higher as compared with the known calcitonin on the tests upon rate.

Synthesis of the compound [I] can be by the conventional peptide synthesis method, that is to say, an amino acid and/or peptide consisting of 2 - 4 amino acids is reacted by condensation in the order of the amino acid sequence of formula [I], and the amino acid construction unit which contains the sequence of the formula

is subjected to ring formation at any stage of construction of the peptide unit, and the protective group for the reactive group is released at any stage of the reaction. If desired the product may be converted to its acid addition salt or complex.

The protective groups for the synthesis of the starting materials or intermediates are conventional protective groups for peptide synthesis and should be easily removable by hydrolysis, acid decomposition, reduction, aminolysis or hydrazinolysis.

For example, the amino group may be protected conventionally by an acyl group such as formyl, trifluoroacetyl, phthaloyl, benzensulfonyl, p-toluenesulfonyl, o-nitrophenylsulfenyl or 2,4-dinitrophenylsulfenyl group; an aralkyl group such as benzyl, diphenylmethyl or triphenylmethyl (these groups may optionally substituted with a lower alkoxy group such as o-methoxy or p-methoxy); a benzyloxycarbonyl group such as benzyloxycarbonyl, o-bromobenzyloxycarbonyl, p-bromobenzyloxycarbonyl, o-chlorobenzyloxycarbonyl, p-nitrobenzyloxycarbonyl, p-methoxybenzyloxycarbonyl, p-phenylazo-benzyloxycarbonyl or p-(p'-methoxyphenylazo)-benzyloxycarbonyl; an aliphatic oxycarbonyl group such as cyclopentyloxycarbonyl, trichloroethyloxycarbonyl, t-amyloxycarbonyl, t-butoxycarbonyl or diisopropylmethoxycarbonyl, or an aralkyloxycarbony group such as 2-phenylisopropoxycarbonyl, 2-torylisopropoxycarbonyl or 2-p-diphenyl-isopropoxycarbonyl. These amino groups can be protected by forming enamin reacted with 1,3-diketone such as benzoylacetone, acetylacetone or dimedone.

The carboxyl group can be protected by its amide formation, hydrazide formation or esterification. The amide group is substituted with a 3,4-dimethoxybenzyl or bis-(p-methoxyphenyl)-methyl group. The hydrazide group is substituted with a benzyloxycarbonyl, trichloroethyloxycarbonyl, trifluoroacetyl, t-butoxycarbonyl, trityl or 2-p-diphenyl-isopropoxycarbonyl group. The ester group is substituted with an alkanol such as methanol, ethanol, t-butanol or cyanomethylalcohol; an aralkanol such as benzylalcohol, p-bromobenzylalcohol, p-chlorobenzylalcohol, p-methoxybenzylalcohol, p-nitrobenzylalcohol, 2,4,6-trimethylbenzylalcohol, benzhydrylalcohol, benzoylmethylalcohol, p-bromobenzoylmethylalcohol or p-chlorobenzoylmethylalcohol; a phenol such as 2,4,6-trichlorophenol, pentachlorophenol, p-nitrophenol, 2,4-dinitrophenol, p-cyanophenol or p-methanesulfonylphenol; or a thiophenol such as thiophenol, thiocresol or p-nitrothiophenol. The hydroxy group in serine, threonine or tyrosine may optionally be protected by esterification or etherification. A group protected by esterification is, for example, a lower alkanoyl group such as an acetyl group; an aroyl group such as a benzoyl group; or a group derived from carbonyl such as benzyloxycarbonyl or ethyloxycarbonyl. A group protected by etherification is, for example, a benzyl, tetrahydropyranyl or t-butyl group. Protection of the hydroxy group can be effected by a 2,2,2-trifluoro-1-t-butyloxycarbonylaminoethyl or 2,2,2-trifluoro-1-benzyloxycarbonylaminoethyl group. However it is not always necessary to protect these hydroxy groups.

The amino group or guanidino group in arginine can be protected by a nitro, tosyl or benzyl oxycarbonyl group, however the guanidino group does not always require protection. The imino group in histidine can be protected by a benzyl, trityl, benzyloxycarbonyl, tosyl, admantyloxycarbonyl, 2,2,2-trifluoro-1-t-butyloxycarbonylaminoethyl or 2,2,2-trifluoro-1-benzyloxycarbonylaminoethyl group, although the imino group does not always require to be protected.

The peptides of the starting materials or intermediates are synthesized by condensation of amino acids or peptides—preferably of two to four amino acids—in the order of the amino acid sequence of formula [I]. For example, an amino acid or peptide having a protected α-amino group and activated terminal carboxyl group is reacted with an amino acid or peptide having free α-amino group and protected terminal carboxyl group. On the other hand, an amino acid or peptide having activated α-amino group and protected terminal carboxyl group is reacted with amino acid or peptide having free terminal carboxyl group and protected α-amino group.

The carboxyl group can be activated by, for example, an acid azide, acid anhydride, acid imidazolide or active ester, such as by converting to cyanomethyl ester, thiophenylester, p-nitrophenylester, p-nitrothiophenylester, p-methanesulfonylphenylester, thiodylester, 2,4-dinitrophenylester, 2,4,5-trichlorophenylester, 2,4,6-trichlorophenylester, pentachlorophenylester, N-hydroxyphthalimidoester, 8-hydroxypiperidine ester or N-hydroxypiperidine ester, carbodiimide, N,N'-carbonyldiimidazol or an isoxazolium salt such as Woodward reagent.

The carboxyl group can be activated in a conventional way by, for example, an acid azide, acid anhydride, active ester or carbodiimide.

Preferred condensation reactions are the Wunsch method, azide, active ester or Geiger methods. In the condensation reaction, racemization should carefully be avoided.

The construction unit including the thus obtained peptide of the formula

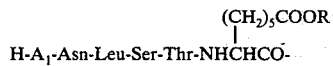

H-A₁-Asn-Leu-Ser-Thr-NHCHCOwherein $A_1$ and R have the same meanings hereinbefore, is provided by the reaction for ring formation. The ring formation reaction is performed by a condensation reaction with activated ω-carboxyl group in α-amino suberic acid and free amino group in N-terminal amino acid. In the condensation reaction the hydroxyl group of serine and threonine is preferably protected.

The preferred process of the present invention is preceded by a condensation reaction with a peptide ring (having optionally protected active groups) containing α-amino suberic acid and the remaining other large peptide having optionally protected active groups. That is to say, the N-terminal fragment consisting of the first to sixth – ninth amino acid is condensed with the residual peptide of the total sequence of seventh – tenth to thirty-first amino acids. To promote reactivity of both fragments at condensation and to prevent racemization, glycine is preferably used as the C-terminal amino acid.

In the present invention it is preferable that a peptide consisting of first – ninth amino acid sequence is reacted with a peptide consisting of 10th – 31st amino acid sequence.

The said condensation reaction can be achieved by starting from the peptide having free terminal carboxyl group, the so-called Wunsch method, or by analogous methods. Also it can preferably be achieved by the azide method starting from the peptide having an azide or hydrazide terminal, by the active ester method, or by the mixed anhydride method.

The synthesis of N-terminal fragment, such as nonapeptide consisting of first to ninth amino acid sequence will be explained in detail in the following, however hexapeptide 1–6, heptapeptide 1–7, or octapeptide 1–8 can also be produced by substantially the same process.

The nonapeptide sequence can be produced by connecting each amino acid with lower peptide consisting of 2–4 amino acids in the order of amino acid sequence from C-terminal amino acid. An amino acid such as glycine, leucine, valine, α-amino suberic acid, threonine, methionine, serine or asparagine is preferably condensed by the active ester method. The lower peptide such as tripeptide 2–4 is preferably condensed by the Geiger method or by the Wünsch method.

In the condensation reaction by the azide, active ester or acid anhydride method, it is not necessary to protect the terminal carboxyl group in nonapeptide. The carboxyl group can also be protected by esterification by alcohols such as methanol, benzyl alcohol or other alcohols. The ester group such as methyl ester can be removed by dilute sodium hydroxide solution or by conversion to hydrazide, and the benzyl ester group can be removed by catalytic hydrogenation. The amino group of the intermediate is protected by a conventional protective group, such as a benzyloxycarbonyl, trityl, t-butoxycarbonyl or 2-p-diphenyl-isopropoxycarbonyl group. The carboxyl group can be protected, if required, by conventional esterification. The hydroxyl group in serine and threonine can be protected, if necessary, by esterification using t-butanol, benzyl alcohol or other alcohol.

The benzyloxycarbonyl, p-nitrobenzylester and benzyl ester groups are split by catalytic hydrogenation in the presence of palladium carbon. The N-trityl group is split by aqueous acetic acid, and the t-butoxycarbonyl group can be decomposed by trifluoroacetic acid. The o-nitrophenylsulfenyl group is split by hydrogen chloride, hydrogen cyanide or sulfurous acid in organic solvent. The diphenylisopropoxycarbonyl group is split by a mixture of acetic acid-formic acid-water (7:1:2). Methyl ester, ethyl ester or p-nitrobenzyl ester is changed to hydrazide by using hydrazine hydrate. The methyl ester group can be split by dilute sodium hydroxide solution, and t-butyl ester is split by trifluoroacetic acid.

A peptide having C-terminal consisting of amino acid sequence from seventh – tenth to thirty-first, which is condensed with N-terminal peptide hereinabove, is preferably synthesized by connecting C-terminal amino acid (amino acid No. 31) or C-terminal fragment, such as peptide of amino acid sequence 30th–31st, 28th–31st, 25th–31st, 24th–31st or 23rd–31st, with each amino acid or lower peptide consisting of two to four amino acids in the order of foregoing amino acid sequence. For example, C-terminal fragment 10th – 31st can be produced by condensation of amino acids and lower peptides such as dipeptide 28th–29th, dipeptide 26th–27th, tripeptide 20th–22nd, tetrapeptide 15th–18th and tripeptide 10th–12th in the order of amino acid sequence from the C-terminal, by the active ester method or the Geiger method. Preferred protective groups for each group are: α-amino group by t-butoxycarbonyl group; side chain carboxyl group of aspartic acid and glutamic acid by benzyl ester group; ε-amino group of lysine by o-chlorobenzyloxycarbonyl group; hydroxyl group of serine, threonine and tyrosine by benzyl group; and amino group in the guanidine group of arginine and imino group of histidine by tosyl group.

The protective group of C-terminal fragment seventh–10th to 31st having protected α-amino group hereinabove, for example docosapeptide amide of 10th–31st sequence, is removed by a suitable method. For example, the trityl group is split by aqueous acetic acid. Diphenyl isopropoxycarbonyl, benzyloxycarbonyl and t-butoxycarbonyl groups are removed by a mixture of glacial acetic acid, formic acid and water; hydrogenation; and trifluoroacetic acid, respectively.

Thus the hentriacontapeptideamide having protected α-amino group, protected ε-amino group, optionally protected side chain carboxyl group and/or hydroxyl group, is obtained. These protective groups are split by the process hereinbefore described preferably by acid decomposition such as by hydrogen fluoride, and finally the product [I] can be obtained.

In the synthesis of the novel polypeptide of the present invention by the Merrifield solid phase peptide synthetic method, the hydroxy group in serine, threonine and tyrosine can be protected by, for example, benzyl; the imino group in histidine can be protected, for example, by 1-benzyloxycarbonylamino-2,2,2-trifluoroethyl group; the guanidino group in arginine can be protected, for example, by a nitro group; and the side chain in glutamic acid can be protected, for example by a benzyl ester group. The protective group for the α-amino group is, for example, a t-butyloxycarbonyl, o-chlorobenzyloxycarbonyl or o-bromobenzyloxycarbonyl group.

The protected peptide is removed from the carrier resin and the protective group is removed by anhydrous hydrogen fluoride.

One-step removal of all protective groups by hydrolysis using trifluoroacetic acid can be achieved when t-butoxycarbonyl group is used for amino group protection; t-butyl ester for side-chain carboxyl group protection; t-butyl ether for hydroxyl group protection in serine; and threonine, tyrosine and 2,2,2-trifluoro-1-t-butoxycarbonylaminoethyl group for imino group protection in histidine.

The novel polypeptide [I] of the present invention can be obtained in the form of a free base or a salt thereof. The free base may conventionally be obtained from its salt. The free base can be changed to its pharmacologically acceptable salt by reacting with an inorganic acid such as hydrochloric acid, hydrobromic acid, sulfuric acid, or phosphoric acid, or an organic acid such as formic acid, acetic acid, propionic acid, glycole acid, lactic acid, pyruvic acid, oxalic acid, succinic acid, malic acid, citric acid, tartaric acid, benzoic acid, benzenesulfonic acid or toluenesulfonic acid.

The novel polypeptide can be converted into a complex thereof by addition of various inorganic or organic substances. The said complex form is composed by adding a kind of inorganic or organic substance to a long chain polypeptide, the complex having a long term activity when administered. Examples of the said complex-forming substance are inorganic compounds derived from metals such as calcium, magnesium or zinc, especially phosphate, pyrophosphate or polyphosphate of the said metals. Further examples of the said complex-forming organic substance are non-antigenic gelatine, CMC, polyglutamic acid or the like.

The abbreviations in this invention have the following meanings.

BOC : t-butoxycarbonyl,
Cbz : benzyloxycarbonyl,
Bzl : benzyl,
OEt : ethyl ester,
OBzl : benzyl ester,
OSU : N-hydroxysuccinylimide ester,
Ser : L-serine,
Leu : L-leucine,
Val : L-valine,
Arg : L-arginine,
Ala : L-alanine,
Lys : L-lysine,
Glu : L-glutamic acid,
Tyr : L-tyrosine,
Phe : L-phenylalanine,
TFA : trifluoroacetic acid,
CHA : cyclohexylamine,
THF : tetrahydrofuran,
AcOEt : ethyl acetate,
WSC : N-ethyl-N'-dimethylaminopropyl-carbodiimide,
HOSU : N-hydroxysuccinylimide,
MeOH : methanol,
AcOH : acetic acid.
AOC : t-amyloxycarbonyl,
ClCbz : o-chlorobenzyloxycarbonyl,
Tos : tosyl,
OBu : t-butyl ester,
ONP : p-nitrophenyl ester,
Asn : L-asparagine,
Thr : L-threonine,
Pro : L-proline,
Asp : L-aspartic acid,
Gly : glycine,
Gln : L-glutamine,
His : L-histidine,
Met : L-methionine,
Ile : L-Isoleucine,
TosOH : p-toluenesulfonic acid,
DCHA : dicyclohexylamine,
DMF : dimethylformamide,
DCC : dicyclohexylcarbodiimide,
HOBT : 1-hydroxybenzotriazole,
EtOH : ethanol, The following examples illustrate the present invention but are not to be construed as limiting the scope thereof as the scope defined by the appended claims.

The assay method for serum calcium reducing activity, the carrier and developing system for thin layer chromatography and conditions for amino acid analysis are as follows:

ASSAY METHOD

Sample is diluted adequately with 0.1 N sodium acetate - 0.1% albumin solution. Male rats are subjected individually to intravenous injection with 0.2 ml. of the respective diluted solutions. After 1 hour, all the rats are killed to obtain their respective blood, and serum calcium value of each blood sample is determined by atomic absorption spectrophotomery. On the other hand, Research Standard B, which is an extract obtained from the thyroid gland of the hog, is diluted so as to give dilutions of 2.5, 5, 10 and 20 MRC mU/0.2 ml. respectively. Male rats are subjected to intravenous injection with 0.2 ml. of the respective diluted solutions. Following the same procedure as above, the serum calcium value of the rats is determined one hour after injection. From the potency of the corresponding Research Standard, the potency of the calcitonin in the sample is determined.

THIN LAYER CHROMATOGRAPHY (TLC)

Carrier: silica gel G.
Solvent system for developer:

| | | |
|---|---|---|
| 1. $CHCl_3$—MeOH—AcOH | 95 : 5 : 3 | |
| 2. $CHCl_3$—MeOH—AcOH | 85 : 15 : 5 | |
| 3. $CHCl_3$—MeOH—AcOH | 85 : 10 : 5 | |
| 4. $CHCl_3$—MeOH—AcOH | 80 : 25 : 2 | |
| 5. $CHCl_3$—EtOH—AcOEt | 5 : 2 : 5 | |
| 6. $CHCl_3$—MeOH—AcOH—$H_2O$ | 10 : 10 : 1 : 1 (lower layer) | |
| 7. Benzene—AcOEt | 2 : 1 | |
| 8. n-BuOH—pyridine—AcOH—$H_2O$ | 15 : 10 : 3 : 12 | |
| 9. methanol | | |

AMINO ACID ANALYSIS

Sample is hydrolyzed with 6 N HCl (with addition of a few drops of anisole) at 110° C., for 40 – 45 hours, and dried out under reduced pressure, then is subjected to amino acid analysis.

EXAMPLE 1

Production of:

$$\overbrace{\text{CO-Ser-Asn-Leu-Ser-Thr-HNCHCO}}^{(CH_2)_5}\text{-Val-Leu-}$$
Gly-Lys-Leu-Ser-Gln-Glu-Leu-His-Lys-Leu-
Gln-Thr-Tyr-Pro-Arg-Thr-Asp-Val-Gly-
Ala-Gly-Thr-Pro-$NH_2$ 1 g. (0.27 mmole)ofBOC-Lys(cl Cbz)-Leu-Ser(Bzl)-
Gln-Glu(OBzl)-Leu-His-Lys(Cl Cbz)-
Leu-Glh-Thr(Bzl)-Tyr(Bzl)-Pro-Arg
(Tos)-Thr(Bzl)-Asp(OBzl)-Val-Gly-
Ala-Gly-Thr(Bzl)-Pro-$NH_2$ 1 g. of (0.27 m mole) of BOC-Lys (Cl Cbz)-Leu-Ser (Bzl)-Gln-Glu (OBzl)-Leu-His-Lys (Cl Cbz)-Leu-Gln-Thr (Bzl)-Tyr (Bzl)-Pro-Arg (Tos)-Thr (Bzl)-Asp (OBzl)-Val-Gly-Ala-Gly-Thr (Bzl)-Pro-$NH_2$ was dissolved in 10 ml. of TFA at −5° C. under reduced pressure and added 1 ml. of 4N HCl/dioxane. After stirring for 40 minutes at room temperature, the solution was concentrated in vacuo and ethyl ether was added thereto to form a precipitate. The precipitate was dried over sodium hydroxide. The dried precipitate was dissolved in 5 ml. of DMF and adjusted to pH 7 with addition of triethylamine under cooling. To that solution was added water to form a precipitate. The precipitate was dried over $P_2O_5$ to obtain de-BOC compound as free base. 400 mg. of $$\overbrace{\text{CO-Ser(Bzl)-Asn-Leu-Ser(Bzl)-Thr(Bzl)-HNCHCO}}^{(CH_2)_5}\text{-Val-Leu-Gly-OH}$$

were dissolved in 2 ml. of DMF. HOSU (90 mg.) was added thereto and further DCC (120 mg.) was added under cooling, then stirred overnight. After reaction, precipitated urea was removed, and to the thus-obtained solution was added the de-BOC free base obtained hereinabove, further DMF (5 mg.) was added to dissolve the compound. After 3 days water was added thereto. The thus-formed precipitate was collected by filtration, washed thoroughly with ethyl acetate and ethyl ether, then dried to obtain 1.4 g. of $$\overbrace{\text{CO-Ser(Bzl)-Asn-Leu-Ser(Bzl)-Thr(Bzl)-HNCHCO}}^{(CH_2)_5}\text{-Val-Leu-Gly-Lys(ClCbz)-}$$
Leu-Ser(Bzl)-Gln-Glu(OBzl)-Leu-His-Lys(ClCbz)-Leu-Gln-Thr(Bzl)-Tyr(Bzl)-
Pro-Arg(Tos)-Thr(Bzl)-Asp(OBzl)-Val-Gly-Ala-Gly-Thr(Bzl)-Pro-$NH_2$ as crude product. The above 1.4 g. of crude material were treated with hydrogen fluoride and 15 ml. of a mixture of phenol and anisole (1:1) at 0° C. for 90 minutes. After distillation of hydrogen fluoride, the residue was washed with ethyl acetate and benzene to solidify the product and dissolved in a 1 molar solution of acetic acid. The solution was passed through a column of Dowex 1 × 1 (acetate form) and the eluate was freeze-dried to obtain 870 mg. of the powder.

870 mg. of this powder were purified by the steps of Sephadex G-50 gel filtration, CM-cellulose ion chromatography and Sephadex LH-20 gel filtration to obtain 200 mg. (3450 MRC U/mg.) of the product.

Rf = 0.71 [carrier: Merck cellulose, developer: n-BuOH - pyridine - AcOH - water (15:10:3:12)].

Amino acid analysis: Lys 0.91 × 2, His 0.92, Arg 0.93, Asp 1.02 × 2, Thr 0.73 × 4, Ser 1.00 × 3, Glu 1.00 × 3, Pro 0.99 × 2, Gly 0.92 × 3, Ala 1.11, Val 0.90 × 2, Leu 0.78 × 5, Tyr 0.96, α-amino suberic acid 0.97.

The starting material is produced as follows:
Production of partial amino acid sequence 10 - 31: BOC-Lys(ClCbz)-Leu-Ser(Bzl)-Gln-Glu(OBzl)-Leu-His-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-$NH_2$ (1) Preparation of BOC-Thr(Bzl)-Pro-$NH_2$
BOC-Thr(Bzl)-OH (67.7 g.), H-Pro-$NH_2$.HCl (33.0 g.) and HOBT (29.6 g.) were added in THF (220 ml.). WSC (40.0 ml.) was added thereto under cooling at −5° C., stirred for 1 hour at −5° C. and then overnight at room temperature. The reaction mixture was concentrated in vacuo and ethyl acetate (800 ml.) was added to the residue, which is then washed twice with 1 N HCl (400 ml.) and twice with 5% sodium bicarbonate solution (300 ml.) and water. After dehydration by anhydrous magnesium sulfate, the organic layer was concentrated in vacuo. The oily material was charged for silicagel (450 g.) column chromatography. Developing by a mixture of benzene - ethyl acetate (1:1), ethyl acetate and methanol is this order and eluting fractions were checked by silica gel thin layer chromatography. Active fractions were collected and dissolved in ethyl acetate (500 ml.) then washed twice with 5% aqueous sodium bicarbonate (300 ml.) and water, and after drying with anhydrous magnesium sulfate, concentrated in vacuo. The residue was treated with n-hexane to obtain BOC-Thr-(Bzl)-Pro-NH$_2$ as white powder (54.5 g., Yield: 61.4%). Rf$_1$ = 0.48, $[\alpha]_D^{28}$ = −14.0° (c=1, DMF).

Elemental analysis ($C_{21}H_{31}NO_3$):

|  | C% | H% | N% |
|---|---|---|---|
| found: | 62.04 | 8.01 | 9.90 |
| calculated: | 62.20 | 7.71 | 10.30 |

(2) Preparation of BOC-Ala-Gly-OBzl

BOC-Ala-OH (94.6 g.), H-Gly-OBzl.TosOH (168.8 g.) and HOBT (67.6 g.) were dissolved in THF (450 ml.) and WSC (91.5 ml.) was added thereto, then stirred for 1 hour at 0° C. and overnight at room temperature. The reaction mixture was concentrated in vacuo and the residue was dissolved in ethyl acetate (800 ml.). 1 N HCl (500 ml.) was added, the precipitate was removed by filtration, and the ethyl acetate layer was washed with 1 N HCl (400 ml.), and twice with 5% sodium bicarbonate solution and water in this order, and, after drying with anhydrous magnesium sulfate, concentrated in vacuo. The residue was treated with n-hexane to obtain crude material (152.5 g.) Recrystallization was carried out twice by ethyl acetate - n-hexane to obtain BOC-Ala-Gly-OBzl (144 g., Yield: 85.7%, m.p.: 87° - 88.5° C., TLC: one spot, RF$_1$ = 0.59).

(3) Preparation of BOC-Ala-Gly-OH

BOC-Ala-Gly-OBzl (101 g.) was dissolved in THF (500 ml.) and hydrogenized with 5% palladium/carbon (7 g.). After 6 hours, the catalyst was removed, concentrated, dissolved in THF (800 ml.), then again hydrogenized with 5% palladium/carbon. After 4 hours, the catalyst was removed and concentrated in vacuo, and the residue was solidified by treating with n-hexane. The solid residue was recrystallized by ethyl acetate - THF - n-hexane to obtain BOC-Ala-Gly-OH (72 g., Yield: 97.4%, m.p.: 129° - 132° C.). TLC: one spot (solvent system 3). $[\alpha]_D^{28}$ = −8.87° (c=1, DMF).

Elemental analysis ($C_{10}H_{18}N_2O_5$):

|  | C% | H% | N% |
|---|---|---|---|
| found: | 48.80 | 7.41 | 11.29 |
| calculated: | 48.77 | 7.37 | 11.38 |

(4) Preparation of BOC-Ala-Gly-Thr(Bzl)-Pro-NH$_2$

BOC-Thr(Bzl)-Pro-NH$_2$ (10.0 g.) was added to TFA (30 ml.) at −5° C., stirred for 30 minutes, and concentrated in vacuo. The residue was treated with ether, filtered and dried over sodium to obtain H-Thr(Bzl)-Pro-NH$_2$.TFA. BOC-Ala-Gly-OH obtained in (3) (6.08 g.) and HOBT (3.34 g.) were added in THF (100 ml.) and WSC (4.5 ml.) was added thereto at −5° C. (pH 4.0). After stirring at −5° C. for 1 hour and at room temperature for 7 hours, the mixture was cooled at −5° C., WSC (0.8 ml.) added and the pH adjusted to 4.0, and stirred at −5° C. for 1 hour and at room temperature overnight, and concentrated in vacuo. The residue was dissolved in ethyl acetate (400 ml.), washed with saturated sodium chloride solution, twice with 5% aqueous sodium bicarbonate (100 ml.), 1 N HCl saturated with NaCl (100 ml.) and water (50 ml.), in this order.

The ethyl acetate layer was dried with anhydrous sodium sulfate and the aqueous layer was extracted with chloroform which was washed twice with water to combine with the ethyl acetate layer. The organic layer was condensed in vacuo and the residue was chromatographed using silica gel (150 g.). The column was flushed with ethyl acetate and methanol, and the methanol eluate was condensed in vacuo. n-Hexane was added to the residue to crystallize the BOC-Ala-Gly-Thr(Bzl)-Pro-NH$_2$. (m.p.: 106° - 116° C., 11.5 g., Yield: 87.3%).

TLC: one spot, Rf$_5$ = 0.29, Rf$_6$ = 0.52.

(5) Preparation of BOC-Val-Gly-OEt

BOC-Val-OH.DCHA (219.2 g.) was added to ethyl acetate (1 liter). The solution was washed twice with 1 N HCl (600 ml.) and water (500 ml.) in this order. After drying with anhydrous sodium sulfate, the solution was concentrated in vacuo. THF (100 ml.) and dichloromethane (400 ml.) were added to the residue and H-Gly-OEt.HCl (69.8 g.) and triethylamine (70 ml.) added thereto. DCC (103.2 g.) was added thereto at −5° C. and stirred at −5° C. for 1 hour and at room temperature overnight. Acetic acid (10 ml.) was added to the reaction mixture, stirred for 1 hour and a filtrate obtained. The filtrate was washed twice with 1 N HCl (500 ml.), twice with 5% sodium bicarbonate solution (500 ml.) and water in this order, and after drying with anhydrous sodium sulfate, concentrated in vacuo. The residue was recrystallized three times using ethyl acetate - n-hexane to obtain BOC-Val-Gly-OEt (105.4 g.), m.p.: 95° - 96° C. Yield: 69.7%.

(6) Preparation of BOC-Val-Gly-OH

BOC-Val-Gly-OEt (96.8 g.) was dissolved in methanol (150 ml.) and 1 N NaOH solution (368 ml.) at −5° C. was added thereto. After 1 hour of stirring, the pH was adjusted to 8.0 by addition of 1 N HCl. Methanol was removed by concentration in vacuo and the aqueous layer was washed with ethyl ether (100 ml.). The aqueous layer was adjusted to pH 2.0 by addition of 1 N HCl. The aqueous layer was extracted four times with ethyl acetate (200 ml.), and the extract was dried using anhydrous sodium sulfate and thereafter concentrated in vacuo. The residue was treated with n-hexane and recrystallized from ethyl acetate - n-hexane to obtain BOC-Val-Gly-OH (85.5 g., Yield: 97.4%). m.p.: 112° - 117° C. (decomp.), TLC: one spot, Rf$_1$ = 0.35.

(7) Preparation of BOC-Val-Gly-Ala-Gly-Thr(Bzl)-Pro-NH$_2$

BOC-Ala-Gly-Thr(Bzl)-Pro-NH$_2$ (10.5 g.) was added to TFA (35 ml.) at −5° C., and, after stirring for 30 minutes, concentrated in vacuo. The residue was treated with ethyl ether, and the precipitated material was filtered and dried in vacuo over sodium hydroxide to obtain H-Ala-Gly-Thr(Bzl)-Pro-NH$_2$.TFA. THF (100 ml.) was added thereto, and triethylamine was added at −5° C. to adjust the pH to 5.0. BOC-Val-Gly-OH (5.49 g.) and HOBT (2.66 g.) were added thereto. To this mixture WSC (3.61 ml.) was added dropwise at −5° C., and the mixture stirred at −5° C. for 1 hour and at room temperature overnight. The reaction mixture was concentrated in vacuo, and the residue was dissolved in chloroform (300 ml.). The solution was washed twice with NaCl-saturated 1 N HCl (200 ml.), twice with NaCl saturated 5% sodium bicarbonate solution (200 ml.) and saturated NaCl solution (75 ml.) in this order. After the solution was dried with anhydrous sodium sulfate, the organic layer was concentrated in vacuo. Recrystallization from methanol - ethyl ether gave BOC-Val-Gly-Ala-Gly-Thr(Bzl)-Pro-NH$_2$ (12.0 g., Yield: 88.3%). m.p.: 121° - 135° C. (decomp.). TLC: one spot. (solvent system 6).

$[\alpha]_D^{28} = -10.30°$ (c = 1, DMF).

Elemental analysis (C$_{33}$H$_{51}$N$_7$O$_9$.½H$_2$O):

|  | C% | H% | N% |
|---|---|---|---|
| found: | 56.67 | 7.43 | 13.90 |
| calculated: | 56.72 | 7.50 | 14.03 |

(8) Preparation of BOC-Asp(OBzl)-Val-Gly-Ala-Gly-Thr(Bzl)-Pro-NH$_2$

TFA (100 ml.) was added to BOC-Val-Gly-Ala-Gly-Thr(Bzl)-Pro-NH$_2$ (33.1g.) at −5° C.; stirred for 30 minutes and concentrated in vacuo. Ethyl ether was added to the residue and the precipitated material was dried in vacuo over NaOH. DMF (80 ml.) was added and triethylamine was further added to adjust the pH to 7.5. After adding HOBT (950 mg.) and BOC-Asp(OBzl)-OSU (30.2 g.) thereto, the pH was adjusted to 7.5 by adding N-methylmorpholine and the mixture stirred for 2 days. The pH was adjusted during stirring, to pH 7.5, by adding N-methylmorpholine, then adding BOC-Asp(OBzl)-OSU (2.0 g.) again, adjusting the pH to 7 by addition of N-methylmorpholine, and the mixture was stirred overnight. A large amount of water was added to the reaction mixture, and the precipitated sticky substance was separated by decantation to crystallize by treatment with ethyl ether. The aqueous layer was extracted with chloroform and the extract was concentrated in vacuo. The residue was treated by addition of water to precipitate a sticky substance. The precipitated sticky substance was crystallized by treatment with ethyl ether. The solids were combined and recrystallized from methanol - ethyl ether four times, and washed with hot ethyl acetate - ethyl ether, then dried to obtain BOC-Asp(OBzl)-Val-Gly-Ala-Gly-Thr(Bzl)-Pro-NH$_2$ (34.2 g., Yield: 79.6%, m.p.: 195° - 199° C.). TLC: one spot. Rf$_5$ = 0.46, $[\alpha]_D^{28} = -18.27°$ (c = 1, DMF).

Elemental analysis (C$_{44}$H$_{62}$N$_6$O$_{12}$.H$_2$O):

|  | C% | H% | N% |
|---|---|---|---|
| found: | 58.05 | 6.90 | 12.47 |
| calculated: | 57.88 | 7.07 | 12.27 |

(9) Preparation of BOC-Thr(Bzl)-Asp(OBzl)-Val-Gly-Ala-Gly-Thr(Bzl)-Pro-NH$_2$

TFA (30 ml.) was added to BOC-Asp(OBzl)-Val-Gly-Ala-Gly-Thr(Bzl)-Pro-NH$_2$ (7.2 g.) at −5° C.; stirred for 30 minutes and concentrated in vacuo. The residue was treated by adding ethyl ether, and the precipitated material was dried in vacuo over NaOH. DMF (15 ml.) was added thereto and the pH adjusted to 7.5 by addition of triethylamine. After adding HOBT (100 mg.) and BOC-Thr(Bzl)-OSU (4.0 g.), the pH was adjusted by N-methylmorpholine and the mixture stirred for 2 days at room temperature. The pH was adjusted further by DMF (3 ml.) and N-methylmorpholine to 7.5 and the mixture stirred overnight.

After the reaction was complete, a large amount of water was added thereto and the precipitated material was filtered and recrystallized from methanol - ethyl ether three times to obtain BOC-Thr(Bzl)-Asp(OBzl)-Val-Gly-Ala-Gly-Thr(Bzl)-Pro-NH$_2$ 6.7 g., Yield: 77.1%, m.p.: 172° - 188° C.). TLC: one spot (solvent system 3 and 6). $[\alpha]_D^{28} = -13.65°$ (c = 1, DMF).

Elemental Analysis (C$_{55}$H$_{75}$N$_9$O$_{14}$.½H$_2$O).

|  | C% | H% | N% |
|---|---|---|---|
| found: | 60.31 | 6.92 | 11.58 |
| calculated: | 60.31 | 7.00 | 11.51 |

(10) Preparation of AOC-Arg(Tos)-Thr(Bzl)-Asp(OBzl)-Val-Gly-Ala-Gly-Thr(Bzl)-Pro-Nh$_2$ TFA (20 ml.) was added at −5° C. to BOC-Thr(Bzl)-Asp(OBzl)-Val-Gly-Ala-Gly-Thr(Bzl)-Pro-NH$_2$ (6.52 g.); stirred for 30 minutes and concentrated in vacuo. The residue was treated by adding ethyl ether and the precipitated substance was dried in vacuo over NaOH. DMF (25 ml.) was added thereto and the pH was adjusted to 5.0 by adding triethylamine at −5° C. HOBT (972 mg.) and AOC-Arg(Tos)-OH (3.2 g.) were added thereto, and WSC (1.3 ml.) was added dropwise under cooling at −5° C., then the mixture stirred for 1 hour at −5° C. and overnight at room temperature. Ethyl acetate was added to the reaction mixture, and the precipitate was treated with hot methanol (400 ml.) - ethyl ether (50 ml.). Thereafter, the mixture was treated with hot methanol (300 ml.) - ethyl ether (100 ml.) to obtain AOC-Arg(Tos)-Thr(Bzl)-Asp(Obzl)-Val-Gly-Ala-Gly-Thr(Bzl)-Pro-NH$_2$ (7.0 g., Yield: 82.7%, m.p.: 187° - 193° C. (decomp.)). TLC: one spot (solvent system 3 and 6). Rf$_3$ = 0.42.

Elemental analysis (C$_{69}$H$_{95}$N$_{13}$O$_{17}$S.H$_2$O):

|  | C% | H% | N% | S% |
|---|---|---|---|---|
| found: | 57.97 | 6.88 | 12.76 | 2.26 |
| calculated: | 58.01 | 6.84 | 12.75 | 2.24 |

Amino acid composition: NH$_3$ 1.28, Arg 0.95 (1), Asp 1.04 (1), Thr 1.50 (2), Pro 0.98 (1), Gly 1.84 (2), Ala 1.00 (1), Val 1.01 (1).

(11) Preparation of BOC-Tyr(Bzl)-Pro-OBzl

BOC-Tyr(Bzl)-OH.CHA (37.6 g.) was mixed with ethyl acetate (300 ml.) and 1 N HCl (120 ml.), separated and the ethyl acetate layer washed three times with water. After drying with anhydrous sodium sulfate, the organic layer was concentrated in vacuo and the oily residue was dissolved in dichloromethane (80 ml.). H-Pro-Obzl.HCl (19.3 g.) was then added thereto and WSC (14.6 ml.) was added to the mixture at −5° C, then the mixture was stirred for 1 hour at −5° C. and overnight at room temperature. The reaction mixture was concentrated in vacuo, and the residue was shaken with ethyl acetate (800 ml.) and 1 N HCl (400 ml.) to separate the ethyl acetate layer. The organic layer was washed twice with 1 N HCl (300 ml.), twice with water (300 ml.), three times with 5% aqueous sodium bicarbonate (300 ml.) and twice with water (300 ml.), in this order. The organic layer was dried with sodium carbonate and concentrated in vacuo. The crude product was subjected to column chromatography using silica gel (400 g.). Chloroform - ethyl acetate (4:1) mixture was passed through the column and the eluates were checked by thin layer chromatography using solvent system 1 to obtain oily BOC-Tyr(Bzl)-Pro-OBzl (43 g.). Rf$_1$ = 0.88.

(12) Preparation of BOC-Thr(Bzl)-Tyr(Bzl)-Pro-OBzl

TFA (50 ml.) was added under cooling at −5° C. in BOC-Tyr(Bzl)-Pro-OBzl (20 g.), stirred for 10 minutes at −5° C. and 50 minutes at room temperature, and concentrated in vacuo. The oily residue was dried over NaOH for one night, DMF (30 ml.) was added and the pH adjusted to 7.5 by addition of triethylamine at −5° C. HOBT (470 mg.) and BOC-Thr(Bzl)-OSU (14.2 g.) were added and the mixture stirred at −5° C. for 1 hour and at room temperature overnight. During stirring, the reaction mixture was maintained at pH 7 by adding N-methylmorpholine. After 2 days, dimethyl amino propylamine (1 ml.) was added and the mixture stirred for a further 2 hours and concentrated in vacuo. The residue was shaken with water (500 ml.) and ethyl acetate (500 ml.) to separate ethyl acetate layer. The aqueous layer was again extracted with ethyl acetate (200 ml.). The ethyl acetate layer was combined, and separately washed with 1 N HCl, water, and 5% sodium bicarbonate solution and water in this order. After dehydration with anhydrous magnesium sulfate, the organic layer was concentrated in vacuo. The residue was crystallized from ethyl ether - n-hexane to obtain crude material (19.6 g.). This crude material was recrystallized from the same solvent to give BOC-Thr(Bzl)-Tyr(Bzl)-Pro-OBzl (14.4 g.: Yield: 54.9%). $Rf_2 = 0.67$.

(13) Preparation of BOC-Thr(Bzl)-Tyr(Bzl)-Pro-OH

BOC-Thr(Bzl)-Tyr(Bzl)-Pro-OBzl (14.2 g.) was dissolved in THF (30 ml.), and 1 N NaOH solution (23 ml.) was added dropwise for 15 minutes at −5° C. After stirring for 4 hours at room temperature, the pH was adjusted to 7 with 1 N HCl addition, then the mixture was concentrated in vacuo to remove THF. Water was added to the aqueous layer and after washing with ethyl ether, the pH of the water layer was adjusted to pH 2 by adding 1 N HCl, then extracted twice with ethyl acetate. The ethyl acetate layer was washed with water and dried by anhydrous magnesium sulfate and concentrated in vacuo. The residue was crystallized from ethyl ether - n-hexane to obtain crude material (12 g.). This crude material was dissolved in ethyl acetate, ethyl ether added thereto and the solution was set aside to crystallize by gradual addition of n-hexane to give BOC-Thr(Bzl)-Tyr(Bzl)-Pro-OH (10.5 g., Yield: 84%, m.p.: 136° - 138° C.). TLC: one spot, $Rf_1 = 0.68$, $Rf_5 = 0.63$.

Elemental analysis ($C_{37}H_{45}N_3O_3$):

|  | C% | H% | N% |
|---|---|---|---|
| found: | 67.33 | 6.85 | 6.40 |
| calculated: | 67.35 | 6.88 | 6.37 |

(14) Preparation of BOC-Thr(Bzl)-Tyr(Bzl)-Pro-Arg(Tos)-Thr(Bzl)-Asp(OBzl)-Val-Gly-Ala-Gly-Thr(Bzl)-Pro-NH₂

AOC-Arg(Tos)-Thr(Bzl)-Asp(OBzl)-Val-Gly-Ala-Gly-Thr(Bzl)-Pro-NH₂ (6.0 g.) was added in TFA (20 ml.) at −5° C., stirred for 30 minutes and concentrated under reduced pressure. The residue was treated with ethyl ether and dried in vacuo over NaOH. DMF (20 ml.) was added and after adjusting the pH to 4.5 by addition of triethylamine at −5° C., HOBT (851 mg.) and BOC-Thr(Bzl)-Tyr(Bzl)-Pro-OH (4.2 g.) were added and WSC (1.2 ml.) was added dropwise at −5° C. Stirring was carried out for 1 hour at −5° C. and overnight at room temperature. Methanol (300 ml.) and ethyl ether (100 ml.) were added to the reaction mixture, and the precipitated material was filtered and recrystallized three times with methanol - ethyl ether, DMF - ethyl ether and methanol - ethyl ether, in this order, to obtain BOC-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (5.9 g., Yield: 71.3%, m.p.: 186.5° - 190° C.). TLC: one spot (solvent system 3 and 6).

$[\alpha]_D^{28} = -15.86°$ (c = 1, DMF).

Elemental analysis ($C_{100}H_{128}N_{16}O_{22}S \cdot \frac{1}{2}H_2O$):

|  | C% | H% | N% | S% |
|---|---|---|---|---|
| found: | 61.44 | 6.63 | 11.55 | 1.73 |
| calculated: | 61.68 | 6.68 | 11.51 | 1.65 |

Amino acid analysis: NH₃ 1.60, Arg 0.92 (1), Asp 1.04 (1), Thr 2.1 (3), Pro 2.08 (2), Gly 1.86 (2), Val 1.00 (1), Tyr 0.91 (1).

(15) Preparation of BOC-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂

BOC-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (5.4 g.) was added to TFA (20 ml.) at −5° C., the mixture stirred for 30 minutes, and concentrated in vacuo. The residue was treated with ethyl ether and dried over NaOH in vacuo. DMF (18 ml.) was added and then triethylamine was added to adjust the pH to 7.5 and HOBT (100 mg.) and BOC-Gln-ONP (1.54 g.) were added, followed by stirring for 2 days at room temperature. During stirring, the pH was maintained at 7.5 by the addition of N-methylmorpholine. Thereafter, BOC-Gln-ONP (0.2 g.) was added and the pH adjusted to 7.0 with stirring overnight. After the reaction, a large amount of water was added to the reaction mixture to precipitate the product, which was recrystallized three times from methanol - ethyl ether to obtain BOC-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (4.8 g., Yield: 82.9%, m.p.: 178° - 182° C.). $Rf_2 = 0.67$, $[\alpha]_D^{28} = -15.19°$ (c = 1, DMF).

Elemental analysis ($C_{105}H_{136}N_{18}O_{24}S \cdot 2H_2O$):

|  | C% | H% | N% | S% |
|---|---|---|---|---|
| found: | 59.92 | 6.56 | 12.05 | 1.47 |
| calculated: | 59.98 | 6.71 | 11.99 | 1.53 |

(16) Preparation of BOC-Lys(ClCbz)-Leu-OEt

BOC-Lys(ClCbz)-OH. t-butylamine salt (7.32 g.) suspended in ethyl acetate was washed three times with 1 N HCl (100 ml.) and water (100 ml.). After drying with anhydrous magnesium sulfate, ethyl acetate was distilled off. To the residue were added dichloromethane (60 ml.), H-Leu-OEt.HCl (2.93 g.) and HOBT (2.0 g.), WSC (2.75 ml.) was further added at −5° C. and the mixture stirred for 1 hour, and further stirred overnight at room temperature. After the reaction, dichloromethane was removed in vacuo, and the residue was dissolved in ethyl acetate (150 ml.). The solution was washed with 1 N HCl, 5% sodium bicarbonate solution and water. After drying with anhydrous magnesium sulfate followed by concentration in vacuo, the residue was recrystallized from ethyl acetate - n-hexane to obtain 6.4 g. of BOC-Lys(ClCbz)-Leu-OEt (Yield: 76.6%, m.p.: 76° - 79° C.).

(17) Preparation of BOC-Lys(ClCbz)-Leu-OH

To a solution of BOC-Lys(ClCbz)-Leu-OEt (6.13 g.) in ethyl acetate (20 ml.) was added 1 N NaOH(12.1 ml.) at 0° C. and the mixture stirred for 2 hours at room temperature. Further 1 N NaOH (1.1 ml.) was added thereto and after one hour of stirring the pH adjusted to 7 and the mixture concentrated in vacuo. The residue was washed with ethyl ether, the aqueous layer adjusted to pH 3 and extracted three times with ethyl acetate (100 ml.). After washing the ethyl acetate layer with water (100 ml.) and drying with anhydrous sodium sulfate, the product was concentrated in vacuo. The residue was dissolved in ethyl ether (50 ml.), concentrated under reduced pressure, and dried to obtain BOC-Lys(ClCbz)-Leu-OH as a powder (5.85 g.).

m.p.: > 46° - 60° C., $[\alpha]_D^{19} = -10.68°$ (c = 1, DMF).

Elemental analysis ($C_{25}H_{38}N_3O_7Cl.\frac{1}{2}H_2O$):

|  | C% | H% | N% |
|---|---|---|---|
| found: | 56.25 | 7.35 | 8.00 |
| calculated: | 56.21 | 7.31 | 7.87 |

(18) Preparation of BOC-Leu-His-OH

H-His-OH.HCl (3.83 g.) was dissolved with heating in water (25 ml.). After cooling to room temperature, sodium bicarbonate (1.84 g.) was added, and, further, HOBT (270 mg.), BOC-Leu-OSU (8.53 g.) and THF (25 ml.) were added. Water (10 ml.) was then added and the mixture stirred overnight at room temperature. The pH of the reaction mixture was adjusted to 7 with addition of aqueous sodium bicarbonate, and BOC-Leu-OSU (1.3 g.) was again added and the mixture stirred. After 6 hours, a further 1.3 g. was added and stirring continued overnight.

After the reaction was found to be complete by checking with TLC, the reaction mixture was concentrated in vacuo to remove organic solvent and the residual aqueous layer was washed with ethyl acetate. The aqueous layer was adjusted to pH 5 and poured into the top of the column of HP-20 (2.3 × 18 cm.), followed by washing with water until the washing eluate showed ninhydrin negative, then eluted with methanol. The eluate was concentrated in vacuo and the residue was treated with ethyl ether. The precipitate formed was recovered by filtration and reprecipitated twice with methanol - ethyl ether to obtain dried powder (3.94 g., Yield: 53.5%, m.p.: 178° - 180° C.).

$[\alpha]_D^{19} = -0.19$ (c = 1, DMF).

Elemental analysis ($C_{17}H_{28}N_4O_5.\frac{3}{4}H_2O$):

|  | C% | H% | N% |
|---|---|---|---|
| found: | 53.39 | 7.65 | 14.71 |
| calculated: | 53.65 | 7.79 | 14.73 |

(19) Preparation of BOC-Leu-Ser(Bzl)-OH

H-Ser(Bzl)-OH (11.7 g.) was dissolved in water (50 ml.) and sodium bicarbonate (10.1 g.) and dioxane (10 ml.) added thereto. BOC-Leu-OSU (16.4 g.) in dioxane (15 ml.) and DMF (5 ml.) were then added. After overnight stirring, the pH of the reaction mixture was adjusted to pH 7, and the mixture concentrated in vacuo to remove organic solvent. The aqueous layer was shaken with ethyl acetate (100 ml.) and the organic layer was washed twice with 1 N HCl and water. The organic layer was dried with anhydrous magnesium sulfate, concentrated in vacuo and the residue was twice recrystallized from ethyl acetate - n-hexane to obtain BOC-Leu-Ser(Bzl)-OH (16.1 g., Yield: 78.8%, m.p.: 82° - 86° C.).

(20) Preparation of BOC-Lys (ClCbz)-Leu-Ser(Bzl)-OH

BOC-Leu-Ser(Bzl)-OH (4.1 g., 10 m mole) was treated at −5° C. with TFA (25 ml.), the mixture stirred for 25 minutes and thereafter concentrated in vacuo. Ethyl ether was added to the residue to precipitate the material, which was dried over NaOH in vacuo.

The crystals were dissolved in DMF (8 ml.) and BOC-Lys(ClCbz)-ONP (8 g.) and HOBT (270 mg.) were added thereto. The pH of the solution was adjusted to pH 8 with N-methylmorpholine then stirred overnight at room temperature. 1 N HCl was added thereto and the precipitate was dissolved in chloroform which was washed three times with 1 HCl, three times with 5% sodium bicarbonate solution and three times with water. After drying with anhydrous magnesium sulfate, the chloroform layer was concentrated in vacuo. The residue was three times reprecipitated from ethyl acetate - n-hexane and a further three times reprecipitated from ethyl ether - n-hexane, then passed through the column of silica gel (180 g.) which was washed with ethyl acetate - benzene (2:1) and eluted with methanol. The methanol eluate was concentrated in vacuo. The residue was recrystallized from ethyl acetate - n-hexane to obtain BOC-Lys (ClCbz)-Leu-Ser(Bzl)-OH [5.25 g., Yield: 74.5%, m.p.: 84° - 100° C. (decomp.)]. TLC : one spot. Amino acid composition: Lys 0.98 (1), Leu 1.00 (1), Ser. 0.82 (1).

(21) Preparation of BOC-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂BOC-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (7.65 g.) was dissolved in TFA (35 ml.) at −5° C., stirred for 30 minutes and concentrated in vacuo. The residue was treated with diethyl ether and the precipitated material was dried over NaOH in vacuo. This was dissolved in DMF (25 ml.), added HOBT (600 mg.), BOC-Lys(ClCbz)-Leu-OH (2.35 g.) and WSC (0.62 ml.) at −5° C. then stirred for 1 hour at −5° C. and thereafter stirred overnight at room temperature. 1 N HCl was added to the reaction mixture to precipitate the material which was reprecipitated twice with methanol - ethyl ether and dried to obtain the product (8.0 g.). Yield: 87.3%.

m.p.:>164° C (decomp.). $[\alpha]_D^{15} = -18.65°$ (c = 1, DMF).

Elemental analysis ($C_{125}H_{164}N_{21}O_{28}SCl.HCl$):

|  | C% | H% | N% |
|---|---|---|---|
| found: | 59.63 | 6.67 | 11.78 |
| calculated: | 59.75 | 6.62 | 11.71 |

(22) Preparation of BOC-Leu-His-Lys(ClCbz)-Leu-Gln-Thr(Bzl)Tyr(Bzl)-Pro-Arg(Tos)-Thr(Bzl)-Asp(OBzl)-Val-Gly-Ala-Gly-Thr(Bzl)-Pro-NH₂

BOC-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (7.68 g.) was dissolved in TFA (40 ml.) under cooling, stirred for 30 minutes and concentrated in vacuo. The residue was treated with ethyl ether, and the precipitate was filtered and dried over NaOH, then dissolved in DMF (20 ml.), adjusted to pH 5 by adding triethylamine, HOSU (430 mg.), BOC-Leu-His-OH (1.37 g.) and WSCO (58 ml.) added at −5° C.

then stirred for one hour, and thereafter overnight at room temperature. 1 N HCl was added to the reaction mixture to precipitate the material which was further reprecipitated from methanol - ethyl ether and repeatedly reprecipitated from DMF - ethyl ether. The product was obtained by drying.

(8.30 g., Yield: 98.2%, m.p.: 167° – 175° C.). $[\alpha]_D^{15} = 17.45°$ (c = 1, DMF).

Elemental analysis ($C_{137}H_{182}N_{25}O_{30}SCl\cdot HCl\cdot 4H_2O$):

|  | C% | H% | N% |
|---|---|---|---|
| found: | 58.19 | 6.71 | 12.42 |
| calculated: | 58.04 | 6.79 | 12.35 |

(23) Preparation of BOC-Glu(OBzl)-Leu-His-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂

BOC-Leu-His-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (7.64 g.) was dissolved in TFA (35 ml.) under cooling, stirred for 40 minutes and concentrated in vacuo. The residue was dissolved in DMF (30 ml.), the pH adjusted to 7 by addition of N-methylmorpholine, then HOBT (70 mg.) and BOC-Glu(OBzl)-OSU (1.82 g.) were added thereto. The pH was again adjusted to pH 7 by addition of N-methylmorpholine and stirred for 2 days at room temperature. 1 N HCl was added to the reaction mixture and the precipitate was recrystallized twice from methanol - ethyl ether to obtain the product after drying. [7.55 g., Yield: 92.5%, m.p.: 161° – 160° C. (decomp.)].

Amino acid analysis Lys 0.94 (1), His 0.83 (1), Arg 1.05 (1), Asp 1.08 (1), Thr 2.53 (3), Glu 2.06 (2), Pro 2.16 (2), Gly 2.00 (2), Ala 1.06 (1), Val 1.10 (1), Leu 1.82 (2), Tyr 0.73 (1).

(24) Preparation of BOC-Gln-Glu(OBzl)-Leu-His-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂

BOC-Glu(OBzl)-Leu-His-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (7.29 g.) was dissolved in TFA (30 ml.) under cooling, stirred for 45 minutes and concentrated in vacuo. The residue was dissolved in DMF (15 ml.), the pH adjusted to 7 by addition of N-methylmorpholine, HOBT (100 mg.) and BOC-Gln-ONP (1.4 g.) added, then stirred overnight at room temperature. 1 N HCl was added to the reaction mixture and the precipitate was collected and washed with water. Reprecipitation was carried out three times to obtain dried product [7.00 g., Yield: 91.5%, m.p.: 171° – 175° C. (decomp)].

(25) Preparation of BOC-Lys(ClCbz)-Leu-Ser(Bzl)-Gln-Glu(OBzl)-Leu-His-Lys(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂

BOC-Gln-Glu(Obzl)-Leu-His-Lys-(ClCbz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂ (6.70 g.) was dissolved in TFA (30 ml.) under cooling, and a 4 N HCl/dioxane (2.2 ml.) added and stirred for 45 minutes at room temperature. The reaction mixture was concentrated in vacuo and ethyl ether added to precipitate the material, which was washed throughly with ethyl ether and dried over NaOH in vacuo.

The substance hereinabove was dissolved in DMF (15 ml.), the pH adjusted to 5.5 to 6 by adding N-methylmorpholine, HOBT (360 mg.), BOC-Lys(ClCbz)-Leu-Ser(Bzl)-OH (1.86 g.) and DCC (540 mg.) dissolved in DMF (5 ml.) added, then the mixture was stirred for 1 hour and overnight at room temperature. 1 N HCl was added and the precipitate formed was collected by filtration. The ethanol-insoluble part of the precipitate and the precipitated material obtained by addition of ethyl ether in the filtrate were combined. Methanol - diethyl ether was added thereto and the precipitate was repeatedly recrystallized from methanol - ethyl ether to obtain the product [7.0 g., Yield: 87.6%, m.p.: 171° – 177° C. (decomp.)]. $[\alpha]_D^{15} = -18.45°$ (c = 1, DMF).

Elemental analysis ($C_{184}H_{242}N_{32}O_{41}SCl\cdot HCl\cdot \frac{1}{2}H_2O$):

|  | C% | H% | N% | Cl% | S% |
|---|---|---|---|---|---|
| found: | 58.53 | 6.65 | 11.83 | 2.64 | 0.94 |
| calculated: | 58.21 | 6.74 | 11.81 | 2.80 | 0.84 |

Amino acid analysis: Lys 1.86 (2), His 0.74 (1), Arg 0.97 (1), Asp 1.04 (1), Thr 2.55 (3), Ser 0.53 (1), Glu 2.85 (3), Pro 2.08 (2), Gly 2.00 (2), Ala 1.04 (1), Val 1.04 (1), Leu 2.67 (3), Tyr 0.67 (1).

Amino acid sequence No. 1 – 9:

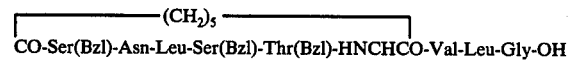

is produced as follows.

(26) Preparation of

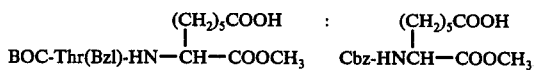

(oil, 56 g.) was dissolved in methanol (300 ml.) and water (150 ml.). To the solution active charcoal was added, and after stirring for 1 hour palladium-carbon was added thereto and hydrogenated for 10 hours. The catalyzer was removed and the solution was concentrated in vacuo up to 100 ml. To that concentrate were added dioxane (200 ml.), triethylamine (21 ml.) under cooling and BOC-Thr(Bzl)-OSU (80 g.). After stirring for 3 days at room temperature, N,N-dimethylamino-1,3-propanediamine was added, stirred for 3 hours, then concentrated up to 100 ml., which was extracted with ethyl acetate. The ethyl acetate layer was washed with 1 N HCl and water, and was distilled in vacuo. The thus-obtained oily product was dissolved in ether and transferred to 5% bicarbonate solution. After carefully washing the aqueous layer with ether, the product was extracted again with ethyl acetate, followed by washing with water, 1 N HCl and water in this order, dehydrated with anhydrous sodium sulfate and the ethyl acetate was distilled off to obtain an oily product (57 g.).

(27) Preparation of

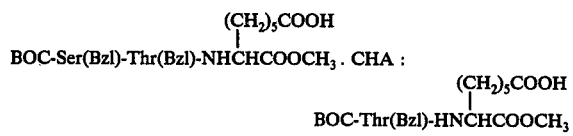

(50 g.) was dissolved in TFA (150 ml.) under cooling. After 30 minutes at room temperature, TFA was removed under reduced pressure and the oily residue was dried over NaOH in vacuo overnight. The oily material was dissolved in DMF (1 ml.), and the pH was adjusted to 6 by addition of triethylamine (40 ml.) under cooling. HOBY (5 g.) and BOC-Ser(Bzl)-OSU (50 g.) were added thereto.

The reaction mixture was adjusted to pH 6 by adding N-methylmorpholine and stirred for 3 days at room temperature. N,N-dimethylamino-1,3-propanediamine was added thereto and the mixture stirred for 1 hour, then water was added and extracted with ethyl acetate. The extract was washed with 1 N HCl, water, 5% sodium bicarbonate and water in this order and dried with anhydrous sodium sulfate. Ethyl acetate was removed and the residue was dissolved in ethyl ether (300 ml.), then re-extracted with 5% sodium bicarbonate solution. The aqueous layer was acidified with HCl, extracted with ethyl acetate and the ethyl acetate layer washed with 5% sodium bicarbonate solution and water, then dried with anhydrous sodium sulfate. After an equal amount of cyclohexylamine was added to the ethyl acetate layer, the mixture was distilled under reduced pressure to obtain oily product which was solidified by adding ether and n-hexane.

Yield; 41 g. m.p.; 70° – 73° C. $[\alpha]_D^{20} = +4.9°$ (c = 2.7, DMF).

(28) Preparation of BOC-Ser(Bzl)-Asn-Leu-NHNH$_2$

BOC-Ser(Bzl)-Asn-Leu-OEt (15 g., 27.2 m mole) was dissolved in methanol (100 ml.). To that solution was added the 80% NH$_2$NH$_2$.H$_2$O (50 ml.) and the mixture was left to stand overnight at room temperature. Ethyl ether was added thereto to precipitate the product completely, and the precipitate was washed with ethyl ether, then recrystallized by MeOH - AcOEt - ethyl ether to obtain the purified product (13.5 g.), (Yield: 92.5%), m.p.; 207° – 209° C. (decomp.), $[\alpha]_D^{20} = 17.4°$ (c = 0.77, DMF).

(29) Preparation of

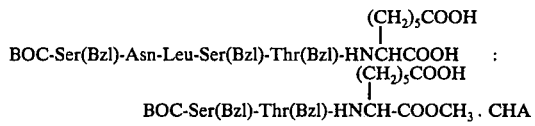

(10.0 g.) was treated with 1 N HCl in ethyl acetate to prepare the free acid, thereafter dried with anhydrous sodium sulfate and concentrated in vacuo. TFA (30 ml.) was added to the oily residue under cooling. After stirring for 30 minutes at room temperature, TFA was removed under reduced pressure. The residue was dried over NaOH in vacuo.

BOC-Ser(Bzl)-Asn-Leu-NHNH$_2$ (8.5 g.) was dissolved in DMF (30 ml.), and dioxane (14 ml.) was added containing 1 N HCl and isoamyl nitrite (3.1 ml.), then reacted for 20 minutes to form the azide.

The dried TFA salt obtained hereinbefore was dissolved in DMF (10 ml.), neutralized with triethylamine, and then slowly added to the solution containing the azide compound at below −40° C. The pH was adjusted to 7 by adding triethylamine and reacted for 3 days at 5° C.

The reaction mixture was slowly added at −5° C. to 0.5 N HCl (300 ml.). The filtered precipitate was washed with water and extracted with chloroform (500 ml.). After washing the chloroform layer with 1 N HCl and aqueous NaCl, chloroform was removed under reduced pressure and the residue was precipitated by adding chloroform - n-hexane to obtain the product (11.8 g.). Yield: 84.3%, m.p.: 183° – 185° C. (decomp.), $[\alpha]_D^{20} = -5.5°$ (c = 0.72, DMF).

Amino acid analysis: Asp 1.00 (1), Thr 0.82 (1), Ser 1.62 (2), Leu 0.91 (1), α-amino suberic acid 1.05 (1).

(30) Preparation of

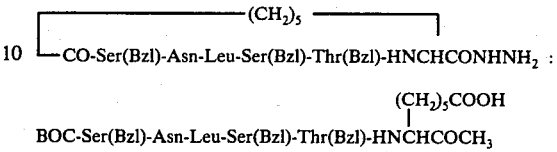

(3.2 g., 3 m moles) was dissolved in dry pyridine (30 ml.), TFA-ONP (5 g.) added, and the mixture stirred for 3 hours at 45° C. The reaction mixture was concentrated in vacuo, and ethyl ether was added. The precipitate was washed with ethyl ether, then dried to obtain a yellowish brown powder (2.9 g.). TFA (20 ml.) was added to this powder under cooling and stirred for 30 minutes at ambient temperature, then the TFA was removed. The residue was dissolved in DMF (20 ml.). The solution was dropwise added to the dry pyridine (2.5 ml.) at 45° C. with stirring for 30 minutes. Stirring was continued for 7 hours at 50° C., and further overnight at room temperature. The reaction mixture was concentrated in vacuo, dissolved in chloroform (2 l.), and washed with saturated aqueous NaCl, 1 N HCl and aqueous NaCl (5 times), in this order, and finally the chloroform layer was concentrated to 10 ml. in vacuo. n-Hexane (500 ml.) was added and the precipitate was collected by filtration to obtain the compound (2.0 g.). Yield: 72%, m.p.: 165° C. (decomp.).

The compound (3.9 g.) was dissolved in DMF (10 ml.) and methanol (50 ml.), 80% NH$_2$NH$_2$.H$_2$O (30 ml.) added and the mixture was stirred overnight at room temperature. After reaction, water was added thereto and the precipitate was filtered, washed with water, then methanol (100 ml.) added and the mixture was refluxed by heating. The reaction mixture was cooled to ambient temperature, and the precipitate was filtered to obtain the product (1.4 g.). $[\alpha]_D^{20} = 8.6°$ (c = 0.8, DMF).

Amino acid analysis: Asp 1.10 (1), Thr (1.00 (1), Ser 1.64 (2), Leu 1.00 (1), α-amino suberic acid 1.08 (1).

(31) Preparation of BOC-Leu-Gly-OBzl

A solution of WSC (34 g.) in dichloromethane (50 ml.) was added dropwise to a suspension of BOC-Leu-OH (46.2 g.), HOBT (1 g.) and H-Gly-OBzl.TosOH (74 g.) in DMF (100 ml.) and dichloromethane (200 ml.) with stirring at −5° C. for 1 hour. After 1 hour, the solution was stirred overnight at room temperature. The reaction mixture was concentrated in vacuo to remove dichloromethane. To the DMF layer was added water and the mixture was extracted with ethyl acetate (1 l.), and again with the same solvent (500 ml.). The ethyl acetate layer was washed with 1 N HCl, water, 5% sodium bicarbonate and water, in this order and dehydrated with sodium sulfate (anhydrous), then concentrated in vacuo to obtain oily BOC-Leu-Gly-OBzl (82 g.) Rf = 0.68.

(32) Preparation of BOC-Val-Leu-Gly-OBzl

TFA (70 ml.) was added to BOC-Leu-Gly-OBzl (76 g.) at −5° C., stirred for 30 minutes and concentrated in vacuo. The residue was dried over NaOH in vacuo. DMF (200 ml.) was added thereto and pH was adjusted to 6.5 by addition of triethylamine (about 50 ml.) at −5° C. BOC-Val-OSU (19 g.) and HOBT (2 g.) are added therein. The reaction mixture was adjusted to pH 6 by adding N-methylmorpholine and stirred for 4 days at room temperature. During the stirring, the pH of the mixture was maintained at pH 6 by adding N-methylmorpholine. A large amount of water was added and extracted with ethyl acetate, N,N-dimethylamino-1,3-propane diamine (1 ml.) was added to the extract, and the mixture stirred for 30 minutes. The extract was washed with water, 1 N HCl, 5% sodium bicarbonate and water, in this order, and dried with anhydrous magnesium sulfate. The ethyl acetate was removed, and the product was crystallized from n-hexane to obtain BOC-Val-Leu-Gly-OBzl (90 g., Yield: 94%). m.p.: 119° − 121° C.

Elemental analysis ($C_{25}H_{39}N_3O_6$):

|  | C% | H% | N% |
|---|---|---|---|
| found: | 62.73 | 8.34 | 8.85 |
| calculated: | 62.86 | 8.25 | 8.80 |

(33) Preparation of

```
    ┌─────────(CH₂)₅─────────┐
CO-Ser(Bzl)-Asn-Leu-Ser(Bzl)-Thr(Bzl)-HNCH-CO-Val-Leu-Gly-OH :
```

```
    ┌─────────(CH₂)₅─────────┐
└─CO-Ser(Bzl)-Asn-Leu-Ser(Bzl)-Thr(Bzl)-HNCHCO-NHNH₂
```

(1.36 g., 1.42 m moles) was suspended in DMF (5 ml.). To that suspension was added dioxane (2 ml.) containing 4 N HCl at −5° C., and completely dissolved at 10° C. Isoamyl nitrite (0.3 ml.) was added at −5° to −10° C. and stirred for 20 minutes. After the reaction, H-Val-Leu-Gly-OH (1.2 g.) was added thereto at −50° C., the pH was adjusted to 7 by adding triethylamine and stirred for 2 days in an ice bath. The reaction mixture was slowly added to 0.5 N HCl (200 ml.) under cooling. The precipitate was washed with 0.5 H NCl and water, then dried to obtain the product (1.5 g.). m.p.: 240° C. (decomp.), Yield: 84.3%, $[\alpha]_D^{20} = -18.4°$ (c = 0.7, DMF).

EXAMPLE 2

Production of

```
    ┌─────────(CH₂)₅─────────┐
└─CO-Ser-Asn-Leu-Ser-Thr-HNCHCO-Val-
Leu-Gly-Lys-Leu-Ser-Gln-Glu-Leu-
His-Lys-Leu-Gln-Thr-Tyr-Pro-Arg-
Thr-Asn-Thr-Gly-Ser-Gly-Thr-Pro-NH₂
```

BOC-Lys(DIP)-Leu-Ser(Bzl)-Gln-Glu(OBzl)-Leu-His-Lys(DIP)-Leu-Gln-Thr(Bzl)-Tyr(Bzl)-Pro-Arg(Tos)-Thr(Bzl)-Asn-Thr(Bzl)-Gly-Ser(Bzl)-Gly-Thr(Bzl)-Pro-NH₂ (500 mg., 0.130 m mole) was dissolved in TFA (5 ml.) and 4 N HCl/dioxane (0.5 ml.) at −5° C. After stirring for 40 minutes at room temperature, the solution was concentrated in vacuo and ethyl ether was added thereto to form a precipitate. The precipitate was dried over NaOH. The dried precipitate was dissolved in DMF (3 ml.), and 2.3 ml. (corresponding to 100 μ mole) of that was concentrated to 1 ml. and the pH adjusted to 7 by adding triethylamine under cooling. To that solution were added HOSU (23 mg.),

```
    ┌─────────(CH₂)₅─────────┐
└─CO-Ser-Asn-Leu-Ser-Thr-HNCHCO-Val-Leu-Gly-OH
```

(90 mg., 90 m mole) and DCC (41 mg.) and the mixture was stirred for 2 days at room temperature. After reaction, 1 M AcOH (150 ml.) was added to precipitate the product, and the thus formed precipitate was collected by filtration, washed thoroughly with water, then dried in vacuo to obtain 520 mg. of the product. The powder (520 mg.) was treated with hydrogen fluoride (50 ml.) and phenol : anisole (1:1) (2 ml.) at 0° C. for 90 minutes. After distillation of hydrogen fluoride, the residue was dissolved in 1 M AcOH. The solution was passed through a column of Dowex 1 × 2 (acetate form), and the eluate was freeze dried to obtain the powder (341 mg.). 341 mg. of this powder dissolved in 0.01 M aqueous ammonium acetate was poured into the top of a column packed with CM-cellulose (2.3 × 50 cm.), and washed with 0.01 M aqueous ammonium acetate (ph 4.5, 700 ml.), and eluted with linear gradient elution by 0.01 − 0.1 mole ammonium acetate (pH 4.5). Each 10 g. of fraction was collected, and the active fractions (fractions Nos. 80 − 111) were collected and freeze dried to obtain the active powder. The lyophilizate was dissolved in 0.1 M AcOH and chromatographed through a column of Sephadez G-50 (2.2 × 105 cm.) by elution with 0.1 M AcOH (10 ml./hour). The eluate (5 g.) was fractionated, then the active fractions (Nos. 55− 63) were collected and lyophilized to obtain the active powder (22 mg.).

The active powder (22 mg.) dissolved in 0.01 M aqueous ammonium acetate was charged on a column packed with CM-cellulose (2.3 × 25 cm.), then was gradiently eluted with 600 ml. of 0.01 mole to 600 ml. of 0.1 mole ammonium acetate (pH 4.5). Each 8 g. of eluted fraction was collected and the active fractions Nos. 109 − 119 were freeze dried. This powder dissolved in a small amount of 0.1 mole acetic acid was poured into the top of a column of Sephadez LH-20 (2.3 × 135 cm.), eluted with 0.1 mole acetic acid, fractions comprising each 6 g. of eluate were taken and the active fractions Nos. 31 − 34 collected which were freeze dried to obtain the active powder.

Rf = 0.61 [Merck cellulose; n-BuOH : pyridine : AcOH : water (15:10:3:12].

Potency : 3025 MRC units/mg.

Amino acid analysis: Lys 1.82 (2), His 0.97 (1), Arg 0.98 (1), Asp 1.96 (2), Thr 4.35 (5), Ser 2.88 (4), Glu 3.00 (3), Pro 2.16 (2), Gly 2.85 (3), Val 1.12 (1), Leu 4.20 (5), Tyr 1.01 (1), α-amino suberic acid 0.99 (1).

We claim:

1. A polypeptide selected from the group consisting of a compound of the formula $$\text{\textemdash CO}\overbrace{\text{\textemdash Ser-Asn-Leu-Ser-Thr-NHCHCO}}^{(CH_2)_5}\text{\textemdash Val-Leu-}$$
Gly-Lys-Leu-Ser-Gln-Glu-Leu-His-Lys-Leu-
Gln-Thr-Tyr-Pro-Arg-Thr-$A_{25}$-$A_{26}$-Gly-$A_{28}$-
Gly-Thr-pro-HN$_2$ wherein $A_{25}$ is Asp or Asn, $A_{26}$ is Val or Thr and $A_{28}$ is Ala or Ser,
and a pharmaceutically acceptable acid addition salt or complex thereof.

2. A polypeptide of the formula $$\text{\textemdash CO-Ser-Asn-Leu-Ser-Thr-HNCHCO-Val-Leu-}^{(CH_2)_5}$$
Gly-Lys-Leu-Ser-Gln-Glu-Leu-His-Lys-Leu-
Gln-Thr-Tyr-Pro-Arg-Thr-Asp-Val-Gly-
Ala-Gly-Thr-Pro-NH$_2$ 3. A polypeptide of the formula $$\text{\textemdash CO-Ser-Asn-Leu-Ser-Thr-HNCHCO-Val-}^{(CH_2)_5}$$
Leu-Gly-Lys-Leu-Ser-Gln-Glu-Leu-
His-Lys-Leu-Gln-Thr-Tyr-Pro-Arg-
Thr-Asn-Thr-Gly-Ser-Gly-Thr-Pro-NH$_2$

* * * * *